United States Patent [19]

Arnaud et al.

[11] Patent Number: 4,585,867

[45] Date of Patent: Apr. 29, 1986

[54] PROCESS FOR THE PREPARATION OF 4-QUINOLINONES

[75] Inventors: Michel Arnaud, Salindres; Jean-Pierre Corbet, Ecully, both of France

[73] Assignee: Rhone-Poulenc Sante, Courbevoie, France

[21] Appl. No.: 652,529

[22] Filed: Sep. 20, 1984

[30] Foreign Application Priority Data

Sep. 22, 1983 [FR] France ............................ 83 15072

[51] Int. Cl.⁴ .......................................... C07D 215/22
[52] U.S. Cl. ............................ 546/153; 260/544 R; 260/544 C; 544/97
[58] Field of Search ........................................ 546/153

[56] References Cited

PUBLICATIONS

Organic Chemistry—Morrison and Boyd, 3rd Edition, pp. 665 and 669.
Hashimoto, Chem. Abstracts 86:190461x.
Johnson, J. Amer. Chem. Soc. 71, pp. 1901–1905 (1949).
Wasserman, J. Org. Chem. 27, pp. 35–39 (1961).

*Primary Examiner*—Donald G. Daus
*Assistant Examiner*—Robert Benson
*Attorney, Agent, or Firm*—Stevens, Davis, Miller & Mosher

[57] ABSTRACT 1,2,3,4-Tetrahydro-4-quinolinones of the formula

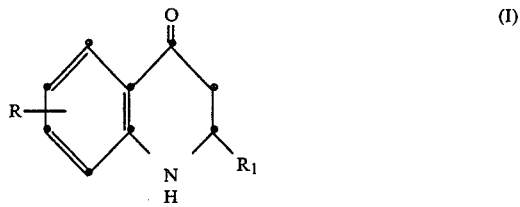

are prepared from a 3-anilinopropionic acid of general for formula

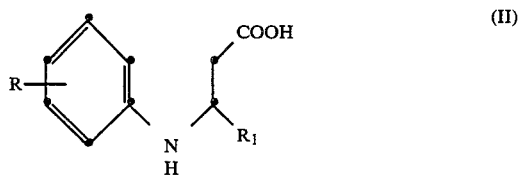

which is treated successively with phosgene, with a base or by heating, and then with a Lewis acid or a strong acid. In the formulae (I) and (II), R denotes a hydrogen atom, a halogen atom, an alkyl radical (1 to 4 carbon atoms) or an alkoxy radical (1 to 4 carbon atoms), and $R_1$ denotes a hydrogen atom or any alkyl radical (1 to 4 carbon atoms). The compounds of formula I are useful as intermediates in the production of known drugs.

7 Claims, No Drawings

PROCESS FOR THE PREPARATION OF 4-QUINOLINONES

The present invention relates to the preparation of 1,2,3,4-tetrahydro-4-quinolinones of the formula:

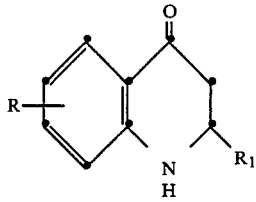

in which R denotes a hydrogen atom halogen atom, a linear or branched alkyl radical of 1 to 4 carbon atoms or a linear or branched alkoxy radical of 1 to 4 carbon atoms, and $R_1$ denotes a hydrogen atom or a linear or branched alkyl radical of 1 to 4 carbon atoms. These compounds are especially useful as intermediates in the synthesis of therapeutically active substances.

It is known that 1,2,3,4-tetrahydro-4-quinolinones of general formula (I) can be prepared by cyclisation of a 3-anilinopropionic acid with polyphosphoric acid according to the process described in French Pat. No. 1,514,280 with an oleum according to the process described in European Pat. No. EP 56,764 or with a hydrofluoric acid/boron trifluoride mixture according to the process described in European Pat. No. EP 56,763.

It should, however, be noted that, in the particular case of the cyclisation of 3-(m-chloroanilino)propionic acid by polyphosphoric acid, a mixture of substantially equal quantities of 5-chloro- and 7-chloro-1,2,3,4-tetrahydro-4-quinolinone is obtained. The selectivity for 7-chloro-1,2,3,4-tetrahydro-4-quinolinone is significantly improved if an oleum or a hydrofluoric acid/boron trifluoride mixture is used as cyclisation agent, but the industrial use of these processes encounters difficulties which result either from the handling of large quantities of sulphuric acid or from the utilisation of a mixture of anhydrous hydrofluoric acid and boron trifluoride.

It has now been found, and this is the subject of the present invention, that the products of general formula (I) can be obtained in good yields and, when the case arises, with increased selectivity, from 3-anilinopropionic acids by carrying out reactions which are simpler than, and have the same high performance as, those previously known.

According to the invention, a 3-anilinopropionic acid of the formula:

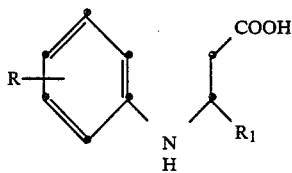

in which R and $R_1$ are defined as above, is treated with phosgene to produce a product of the formula:

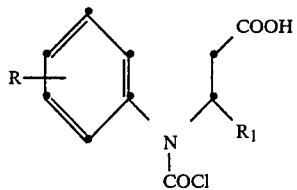

in which R and $R_1$ are as defined above, and the compound of formula III is then converted by the action of a base or by heating, into a compound of the formula:

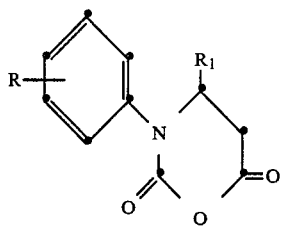

in which R and $R_1$ are as defined above, and the compound of formula IV is then treated with a Lewis acid or a strong acid in a suitable solvent, to give a product of the formula (I).

The compounds of formula (III) are preferably obtained by the action of phosgene on a compound of formula (II) in an organic solvent, such as methylene chloride, 1,1,2-trichloroethane, an aliphatic ester or dioxane, at a temperature between −10° and 150° C. and preferably between 30° and 80° C. Generally, a slight excess of phosgene (less than 10%) is employed relative to the 3-anilinopropionic acid of formula (II). It is advantageous to work in an inert atmosphere.

The compounds of formula (IV) are preferably obtained by the action of a base such as triethylamine or pyridine on a compound of formula (III), or by simply heating a compound of formula (III) to a temperature higher than 50° C., and preferably between 70° and 150° C., in an anhydrous organic solvent which may be an ether, aliphatic ester such as isopropyl acetate, or aliphatic chlorinated solvent such as 1,1,2-trichloroethane.

The compounds of formula (I) are then obtained by intramolecular cyclisation of a compound of formula (IV) with a Lewis acid or a strong acid. The Lewis acid, may be, for example, aluminium chloride, ferric chloride, titanium chloride or stannic chloride. The strong acid is preferably sulphuric acid, hydrofluoric acid, a sulphonic acid such as methanesulphonic acid, polyphosphoric acid, trichloroacetic acid or trifluoroacetic acid.

When a Lewis acid is used, the reaction is carried out in a suitable organic solvent at a temperature between 20° and 60° C. The organic solvent may be a halogenated hydrocarbon such as methylene chloride or 1,1,2-trichloroethane, carbon disulphide, a nitroalkane or tetrachloroethylene.

When a strong acid is used, the cyclisation is performed by heating to a temperature between 20° and 100° C.

The product of general formula (I) can be isolated from the reaction mixture and purified by application of the customary methods.

The compounds of formula (III) and (IV), with the exception of the products in which $R_1$ denotes a hydrogen atom and R denotes a hydrogen atom or a methyl radical in the para-position to the nitrogen atom, are new compounds which form another subject of the present invention.

The acids of the formula (II) used as starting material can be obtained by the action of a suitably substituted aniline on an acid of the formula:

$$R_1-CH=CH-COOH \qquad (V)$$

in which $R_1$ is defined as above. The reaction is generally performed in water at a temperature between 70° and 100° C. employing an excess of the aniline relative to the acid of formula (V). The reaction time is generally between 1 and 4 hours.

The 1,2,3,4-tetrahydro-4-quinolinones of general formula (I) are especially useful as intermediates in the synthesis of therapeutically active substances such as chloroquine, glafenine, antrafenine or amodiaquine. More especially, 7-chloro-1,2,3,4-tetrahydro-4-quinolinone can be converted to chloroquine by condensation with 4-diethylamino-1-methylbutylamine in the presence of air according to the process described by W. S. Johnson and B. G. Buell, J.Amer. Chem. Soc., 74, 4513 (1952).

The Examples which follow show how the invention can be put into practice.

EXAMPLE 1

In a 100 cc round-bottomed flask equipped with magnetic stirring, a thermometer, an acetone/dry ice reflux condenser, a device for introducing gas and a dropping funnel, dry methylene chloride (20 cc) is introduced. Phosgene (3.15 g; 31.8 mmol) is condensed in at a temperature between 0° and 5° C. The reaction mixture is maintained under an atmosphere of argon. There is then introduced, in the course of 19 minutes, a solution of 3-(m-chloroanilino)propionic acid (6.25 g; 31.3 mmol) in methylene chloride (15 cc). The temperature rises from 6° to 23° C. The reaction mixture then consists of a yellow liquid phase and a white precipitate in suspension. The stirring is continued for 10 minutes at 23° C. and then a stream of argon is passed through the reaction mixture for 50 minutes to remove the phosgene which has not reacted.

The precipitate is separated by filtration under a stream of argon and then dried to constant weight under reduced pressure (1 mm Hg; 0.13 kPa). 3-(m-Chloroanilino)propionic acid hydrochloride (3.2 g) is thus obtained.

The filtrate is concentrated to dryness. N-Chloroformyl-3-(m-chloroanilino)propionic acid (4.58 g) is thus obtained almost pure, m.p. 106° C., the structure of which is confirmed by the infrared spectrum, mass spectrum and proton nuclear magnetic resonance spectrum. The product after recrystallisation in isopropyl ether melts at 111° C.

3-(m-Chloroanilino)propionic acid can be prepared in the following manner:

To a mixture of m-chloroaniline (510.3 g) in water (150 cc) maintained under an atmosphere of argon and stirred at 80° C., there is added, in the course of 10 minutes, a solution of acrylic acid (72.05 g) in water (100 cc). The reaction mixture, which consists of two phases, is maintained for 3 hours at 80° C. with stirring, and is then cooled to 20° C. After decantation, the aqueous phase (upper layer) is removed. A 2.6N aqueous caustic soda solution (423 cc) is added to the organic phase while it is stirred, the temperature being maintained at 20° C. After decantation, the organic phase consisting of m-chloroaniline (303 g) is separated. The aqueous phase (850 cc) is extracted successively with ether (6×450 cc).

The aqueous phase, from which the ether is removed by evaporation under reduced pressure (20 mm Hg; 2.7 kPa), is acidified by adding 50% strength (by weight) sulphuric acid (105 g). The final pH is 3.5 (isoelectric point). The temperature rises from 22° to 33° C., and the mixture is then heated to 40° C. After decantation, the following are separated:

a lower organic phase (208.8 g) consisting of melted 3-(m-chloroanilino)propionic acid saturated with water (8.6% of water)

an upper aqueous phase (601 g) containing 3-(m-chloroanilino)propionic acid (2.28 g) and sodium sulphate (156 g).

The organic phase is heated for 1 hour to 80° C. under reduced pressure (20 mm Hg; 2.7 kPa). A product (195.4 g) is obtained which contains 3-(m-chloroanilino)propionic acid (94%) and water (2.3%).

EXAMPLE 2

In a 50 cc round-bottomed flask equipped with magnetic stirring, a water condenser and a dropping funnel, there are introduced, under an atmosphere of argon, dry ethyl ether (25 cc) and then N-chloroformyl-3-(m-chloroanilino)propionic acid (1.06 g; 4.06 mmol). There is then added, in the course of 5 minutes and at a temperature in the region of 20° C., a solution of triethylamine (0.6 cc; 4.3 mmol) in dry ethyl ether (2 cc). A copious white precipitate is formed. After 1 hour 15 minutes of contact, no more starting material remains, according to thin layer chromatography. After filtration and drying of the precipitate to constant weight, a mixture (1.322 g) consisting of triethylamine hydrochloride and 3-(m-chlorophenyl)-2,6-dioxo-1,3-perhydrooxazine is obtained. 1.138 g of the precipitate obtained is suspended in dry ethyl acetate (approximately 20 cc). After filtration, the filtrate is concentrated to dryness.

3-(m-Chlorophenyl)-2,6-dioxo-1,3-perhydrooxazine (0.676 g) is thus obtained, in the form of a white solid, m.p. 126° C., the structure of which is confirmed by the infrared spectrum, mass spectrum and proton nuclear magnetic resonance spectrum.

EXAMPLE 3

In an 50 cc Erlenmeyer flask equipped with a condenser and maintained under an atmosphere of argon, there is introduced 3-(m-chlorophenyl)-2,6-dioxo-1,3-perhydrooxazine (0.334 g; 1.48 mmol) dissolved in methylene chloride (5 cc). In the course of 5 minutes and at a temperature in the region of 20° C., anhydrous aluminium chloride (0.453 g; 3.4 mmol) and methylene chloride (2 cc) are added. A white-yellow suspension is formed first, which redissolves towards the end of the addition of aluminium chloride. After stirring for 1 hour, the starting material has disappeared. The reaction is stopped after 1 hour 30 minutes.

The reaction mixture is poured onto 50 g of ice. The pH of the aqueous phase is between 4 and 5. The organic products formed are extracted by three fractions of methylene chloride. The methylene chloride solution is washed with water and then dried over anhydrous sodium sulphate. After filtration and then evaporation of the filtrate, a pale yellow solid (0.258 g) is obtained.

Analysis of this solid by gas chromatography and by high performance liquid chromatography show that it contains 7-chloro-1,2,3,4-tetrahydro-4-quinolinone (95 to 96%) and 5-chloro-1,2,3,4-tetrahydro-4-quinolinone (0.5%).

The yield is 92% relative to the 3-(m-chlorophenyl)-2,6-dioxo-1,3-perhydrooxazine used.

EXAMPLE 4

In a 20 cc round-bottomed flask equipped with magnetic stirring, a thermometer, a condenser and a dropping funnel, there is introduced 3-m-chlorophenyl-2,6-dioxo-1,3-perhydrooxazine (0.514 g; 2.27 mmol) dissolved in methylene chloride (15 cc). Ferric chloride (0.371 g; 2.28 mmol) is added in a single portion at a temperature in the region of 20° C. The reaction mixture is maintained with stirring for 28 hours at 40° C. After cooling to a temperature in the region of 20° C. and addition of 1N hydrochloric acid (5 cc) and distilled water (20 cc), the organic phase is separated and then washed with distilled water. The methylene chloride solution is then dried over anhydrous sodium sulphate. After filtration and then evaporation of the solvent, an orange residue (0.329 g) is obtained.

An analysis of this residue by gas chromatography shows that it contains 7-chloro-1,2,3,4-tetrahydro-4-quinolinone (33%) and 5-chloro-1,2,3,4-tetrahydro-4-quinolinone (less than 1%).

The yield is 26% relative to the 3-(m-chlorophenyl)-2,6-dioxo-1,3-perhydrooxazine used.

EXAMPLE 5

In a 20 cc round-bottomed flask equipped with magnetic stirring, a thermometer, a condenser and a dropping funnel, there is introduced 3-(m-chlorophenyl)-2,6-dioxo-1,3-perhydrooxazine (0.224 g; 0.990 mmol) dissolved in anhydrous methylene chloride (5 cc). Titanium tetrachloride (0.189 g; 0.910 mmol) is added in a single portion at a temperature in the region of 20° C. The reaction mixture is maintained with stirring for 18 hours at a temperature in the region of 40° C. 1,2-Dichloroethane (5 cc) is then added and the methylene chloride is removed by distillation. The reaction mixture is then maintained with stirring for 54 hours 15 minutes at a temperature in the region of 80° C. After being cooled, the reaction mixture is treated in a similar manner to that described in Example 4. An oily residue (0.172 g) is obtained.

Analysis of this residue by gas chromatography shows that it contains 7-chloro-1,2,3,4-tetrahydro-4-quinolinone (34%) and 5-chloro-1,2,3,4-tetrahydro-4-quinolinone (Less than 1%).

The yield is 31% relative to the 3-(m-chlorophenyl)-2,6-dioxo-1,3-perhydrooxazine used.

EXAMPLE 6

In a 100 cc round-bottomed flask equipped with magnetic stirring, a thermometer, a dry ice/acetone reflux condenser, a device for introducing gas and a dropping funnel, there is introduced 3-(2-methylanilino)propionic acid (5.29 g; 29.6 mmol) and methylene chloride (30 cc). The mixture maintained under an atmosphere of argon is heated to a temperature in the region of 40° C., and phosgene (5.20 g; 52.6 mmol) is then added with stirring in the course of 25 minutes, while maintaining the temperature between 36° C. and 40° C. During the introduction of phosgene, a white precipitate of 3-(2-methylanilino)propionic acid hydrochloride forms. The reaction mixture is heated to a temperature in the region of 40° C. for a further hour. The white precipitate is then almost completely dissolved. After cooling to 20° C. and the removal of the phosgene which has not reacted, the light precipitate which remains is separated by filtration. The filtrate is concentrated to dryness. N-Chloroformyl-3-(2-methylanilino)propionic acid (7 g) is thus obtained almost pure, m.p. 112° C., the structure of which is confirmed by the infrared spectrum, mass spectrum and proton nuclear magnetic resonance spectrum. The product, after recrystallisation in a toluene/hexane mixture (70:30 by volume), melts at 113° C.

3-(2-Methylanilino)propionic acid can be prepared in a manner similar to that described in Example 1 but starting from o-toluidine (64.3 g; 0.60 mole), acrylic acid (11.6 g; 0.16 mole) and water (36 cc).

A white powder (23.85 g) is obtained which, after recrystallisation in a toluene/hexane mixture (70:30 by volume), gives a pure product (21.7 g; 0.12 mole) melting at 87° C.

EXAMPLE 7

By working in a manner similar to that described in Example 2, but starting from N-chloroformyl-3-(2-methylanilino)propionic acid (2.42 g; 10.0 mmol), dry ethyl ether (40 cc) and triethylamine (1.52 cc), a white semi-solid residue (1.25 g) is obtained which consists of almost pure 2,6-dioxo-3-(2-methylphenyl)-1,3-perhydrooxazine.

The product, after recrystallisation in a hexane/ethyl acetate mixture (50:50 by volume), melts between 165° C. and 170° C.

The structure is confirmed by the infrared spectrum, mass spectrum and proton nuclear magnetic resonance spectrum.

EXAMPLE 8

By working in a manner similar to that described in Example 3, but starting from 2,6-dioxo-3-(2-methylphenyl)-1,3-perhydrooxazine (1.06 g; 5.20 mmol), methylene chloride (17 cc) and aluminium chloride (1.70 g), a pale yellow solid (0.84 g) is obtained which melts between 92° C. and 94° C. Analysis of this product by infrared, mass and nuclear magnetic resonance spectrometry shows that it is almost pure 8-methyl-1,2,3,4-tetrahydro-4-quinolinone. The product, after recrystallisation in hexane, melts at 98° C.

EXAMPLE 9

By working in a manner similar to that described in Example 6, but starting from 3-(4-methoxyanilino)propionic acid (2.88 g; 14.7 mmol), methylene chloride (20 cc) and phosgene (4.3 g; 43.5 mmol), almost pure N-chloroformyl-3-(4-methoxyanilino)propionic acid (3.77 g) is obtained in the form of a white powder which melts at 90° C. After recrystallisation in a hexane/ethyl acetate mixture (50:50 by volume), the product melts at 93° C. The structure of the product obtained is confirmed by the infrared spectrum, mass spectrum and proton nuclear magnetic resonance spectrum.

3-(4-Methoxyanilino)propionic acid is prepared in a manner similar to that described in Example 1 but starting from p-anisidine (61 g; 0.495 mole), acrylic acid (9.5 g; 0.132 mole) and water (12 cc). After recrystallisation in toluene, the pure product (11.7 g; 0.060 mole) is obtained in the form of a white powder which melts at 89° C.

EXAMPLE 10

By working in a manner similar to that described in Example 2, but starting from N-chloroformyl-3-(4-methoxyanilino)propionic acid (2.54 g; 9.9 mmol), dry ethyl ether (40 cc) and triethylamine (1.52 cc), a white powder (1.19 g) is obtained which melts at about 140° C. Analysis of this product by infrared, mass and nuclear magnetic resonance spectrometry shows that it is almost pure 2,6-dioxo-3-(4-methoxyphenyl)-1,3-perhydrooxazine. The product, after recrystallisation in a hexane/ethyl acetate mixture (30:70 by volume), melts at about 144° C.

EXAMPLE 11

By working in a manner similar to that described in Example 3, but starting from 2,6-dioxo-3-(4-methoxyphenyl)-1,3-perhydrooxazine (0.65 g; 2.9 mmol), methylene chloride (15 cc) and aluminium chloride (0.79 g; 5.9 mmol), a yellow solid (0.44 g) is obtained which melts at 110° C. Analysis of this product by infrared, mass and nuclear magnetic resonance spectrometry shows that it is almost pure 6-methoxy-1,2,3,4-tetrahydro-4-quinolinone. After recrystallisation in toluene, the product melts at 111° C.

We claim:

1. A process of the preparation of 7-chloro-1,2,3,4-tetrahydro-4-quinolinone which comprises treating 3-(m-chloro-anilino)propionic acid with phosgene to produce N-chloroformyl-3-(m-chloroanilino)propionic acid, converting the said product, by the action of an organic base or by heating, into 3-(m-chlorophenyl)-2,6-dioxo-1,3-perhydrooxazine, and treating the latter with aluminium chloride in an inert organic solvent or with a strong acid, to provide 7-chloro-1,2,3,4-tetrahydro-4-quinolinone.

2. A process according to claim 1, in which the treatment with phosgene is performed in an inert organic solvent at a temperature between −10° and 150° C.

3. A process according to claim 2, in which the solvent is methylene chloride, 1,1,2-trichloroethane, dioxane or an aliphatic ester.

4. A process according to claim 1, in which the conversion by the action of an organic base is performed with triethylamine or pyridine at a temperature between 0° and 30° C.

5. A process according to claim 1, in which the conversion in the absence of a base is performed by heating at a temperature above 50° C. in an anhydrous chlorinated solvent.

6. A process according to claim 1, in which a strong acid is used which is sulphuric acid, hydrofluoric acid, a sulphonic acid, polyphosphoric acid, trichloroacetic acid or trifluoroacetic acid.

7. A process according to claim 1, in which the aluminium chloride is used in a solvent chosen from a halogenated hydrocarbon, carbon disulphide, a nitroalkane or tetrachloroethylene.

* * * * *